United States Patent [19]

Imanari et al.

[11] Patent Number: 4,564,713

[45] Date of Patent: Jan. 14, 1986

[54] PROCESS FOR PRODUCING 4,4'-DIHYDROXYDIPHENYLS

[75] Inventors: Makoto Imanari; Hiroshi Iwane; Takahiro Sugawara, all of Inashiki, Japan

[73] Assignee: Mitsubishi Petrochemical Co., Ltd., Tokyo, Japan

[21] Appl. No.: 690,614

[22] Filed: Jan. 11, 1985

[30] Foreign Application Priority Data

Jan. 23, 1984 [JP] Japan ................................. 59-9856

[51] Int. Cl.$^4$ ..................... C07C 39/14; C07C 39/15
[52] U.S. Cl. ................................................. 568/730
[58] Field of Search ........................................ 568/730

[56] References Cited

U.S. PATENT DOCUMENTS

| | | | |
|---|---|---|---|
| 4,085,124 | 4/1978 | Rutledge | 568/730 |
| 4,100,205 | 7/1978 | Rutledge | 568/730 |
| 4,132,722 | 1/1979 | Rutledge | 568/730 |
| 4,180,686 | 12/1979 | Dodd | 568/730 |
| 4,195,189 | 3/1980 | Earley | 568/730 |
| 4,256,596 | 3/1981 | Cohen | 568/730 |
| 4,354,048 | 10/1982 | Strom | 568/730 |
| 4,438,284 | 3/1984 | Strom | 568/730 |

*Primary Examiner*—Werren B. Lone
*Attorney, Agent, or Firm*—Oblon, Fisher, Spivak, McClelland & Maier

[57] ABSTRACT

A process for producing 4,4'-dihydroxydiphenyls is disclosed, which comprises dimerizing alkylphenols in an aqueous solution of pH 7 to 12 containing a surfactant in the presence of an oxidizing agent, wherein the dimerization is conducted in the presence of a copper compound and a basic boron compound or a mixture of a basic substance and a boron compound. According to this process, the desired 4,4'-dihydroxydiphenyls can be easily obtained in high yield.

9 Claims, No Drawings

PROCESS FOR PRODUCING 4,4'-DIHYDROXYDIPHENYLS

FIELD OF THE INVENTION

The present invention relates to a process for producing 4,4'-dihydroxydiphenyls.

According to the process of the present invention, the desired product 4,4'-dihydroxydiphenyls can be produced easily and in high yield.

The 4,4'-dihydroxydiphenyls produced by the process of the present invention can be used as stabilizers for petroleum products as described in U.S. Pat. No. 2,479,948 as well as starting materials for epoxy compounds.

BACKGROUND OF THE INVENTION

It is known that substituted phenols undergo oxidative coupling to form self-condensation products such as diphenoquinone, 4,4'-dihydroxydiphenyl and polyphenylene oxide.

However, processes for producing 4,4'-dihydroxydiphenyls from alkylphenols as described in, for example, U.S. Pat. No. 4,180,686 and British Pat. No. 2,047,232 require an organic solvent or a stoichiometric amount of an organic reagent. In addition, in these processes, it is difficult to discontinue the oxidative coupling reaction at the stage of 4,4'-dihydroxydiphenyl, and the reaction proceeds to yield diphenoquinone or polyphenylene oxide as a major product.

On the other hand, Japanese Patent Application (OPI) No. 65834/78 (the term "OPI" as used herein refers to a "published unexamined Japanese patent application") discloses a process for producing 4,4'-dihydroxydiphenyl using a copper-amine complex as a catalyst in water. However, this process requires a stirring apparatus having the performance of 6,000 to 10,000 rpm and a special apparatus of a wrinkled Morton flask. Thus, it is difficult to practice such a process on an industrial scale. When this special process is conducted using an industrially practicable apparatus as is employed in the present invention, the conversion of alkylphenol and the yield of 4,4'-dihydroxydiphenyl are low as shown in Comparative Example 1 described hereinafter and those are not satisfactory results.

SUMMARY OF THE INVENTION

As a result of intensive investigations to overcome the above-described defects in the prior art, the present invention has been achieved.

Accordingly, an object of the present invention is to provide a process for producing 4,4'-dihydroxydiphenyls which comprise dimerizing alkylphenols represented by the formula:

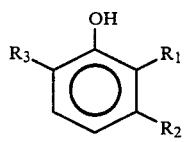

wherein $R_1$ and $R_3$ each represents a straight or branched chain alkyl group having 1 to 12 carbon atoms, and $R_2$ represents hydrogen atom or a straight or branched chain alkyl group having 1 to 12 carbon atoms, in an aqueous solution of pH 7 to 12 containing a surfactant in the presence of an oxidizing agent, wherein said dimerization is conducted in the presence of a copper compound and a material selected from the group consisting of a basic boron compound and a mixture of a basic substance and a boron compound.

The process of the present invention does not require organic solvents and also special stirring apparatus and reactor, and can easily produce the desired product, 4,4'-dihydroxydiphenyl, in high yield.

DETAILED DESCRIPTION OF THE INVENTION

The alkylphenols which can be used in the present invention are 2,6-dialkylphenols or 2,3,6-trialkylphenols represented by the formula:

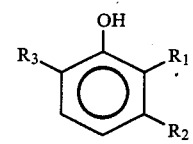

wherein $R_1$ and $R_3$ each represents a straight or branched alkyl group having 1 to 12 carbon atoms, and $R_2$ is a hydrogen atom or a straight or branched chain alkyl group having 1 to 12 carbon atoms.

Examples of the 2,6-dialkylphenols include 2,6-xylenol, 2-methyl-6-butylphenol, 2,6-diethylphenol, 2,6-diisobutylphenol, 2-methyl-6-octylphenol, 2-isobutyl-6-dodecylphenol, 2,6-di-tert-butylphenol, 2,6-di-sec-butylphenol, 2-cyclohexyl-6-methylphenol, etc.

Examples of the 2,3,6-trialkylphenols include 2,3,6-trimethylphenol, 2,3,6-triethylphenol, 2,6-dimethyl-3-ethylphenol, 2,3-diethyl-6-tert-butylphenol, 2,6-di-tert-butyl-3-methylphenol, etc.

In the process of the present invention, a copper compound is used as a catalyst. Either of cuprous compounds and cupric compounds which can generate copper ion in an aqueous solution can be used as the copper compound.

Examples of the copper compounds which can be used in the process of the present invention include the following materials:

(1) halides such as chlorides, bromides and iodides;

(2) basic halohydroxides represented by the formula:

wherein X represents chlorine, bromine, iodine or fluorine;

(3) carboxylates such as acetate, benzoate, etc.;

(4) sulfates;

(5) nitrates;

(6) alkylsulfates and arylsulfates;

(7) carbonates and basic carbonates such as $CuCO_3$—$Cu(OH)_2$, $Cu_2CO_3$—$CuOH$, etc.;

(8) hydroxides; and (9) chlorates such as $CuClO_3$, $Cu(ClO_3)_2$, etc.

In the process of the present invention, the copper compounds are used in an amount of 0.01 to 0.1 mmol, preferably 0.02 to 0.08 mmol, per mol of the alkylphenol. The reaction can take place even when the copper compound is used in an amount smaller than 0.01 mmol, but the reaction rate is too slow and the yield is low. On the other hand, when the copper compound is used in an amount greater than 0.1 mmol, the amount of diphenoquinone by-produced increases.

According to the process of the present invention, the reaction is conducted by adding a surfactant to the reaction system. The term "surfactant" as used herein means an organic compound having both a hydrophobic group and a hydrophilic group in the molecule.

Examples of the surfactant include fatty acid soaps, alkylsulfonates, alkylbenzenesulfonates, alkylnaphthalenesulfonates, alkylsulfates, alkyl ether sulfates, alkyl phosphates, alkyl ether phosphates, etc.

When the surfactant is used in an amount of 0.05 mmol or more, preferably 0.1 to 150 mmols, more preferably 0.5 to 50 mmols, per mol of the alkylphenols, good results can be obtained. Even if the surfactant is used in an amount greater than the above range, the yield of 4,4'-dihydroxydi-phenyl does not increase any more.

In conducting the process of the present invention, the pH of the reaction mixture must be kept in the range of from 7 to 12. To achieve this pH range, a basic substance or a basic boron compound must be added to the reaction mixture. In the case of using the basic substance, a boron compound is also added to the reaction mixture. Where the pH is kept at 7 to 12 as described above, the yield of 4,4'-dihydroxydiphenyl increases.

Examples of the basic boron compound which can be used in the present invention include lithium metaborate, sodium metaborate, sodium perborate, lithium tetraborate, borax, trimethoxyborane, triphenoxyborane, etc.

Examples of the boron compound which can be added in combination with the basic substance include boric acid, boron oxide, etc. in addition to the above-described basic boron compounds.

Examples of the basic substance which can be used to maintain the pH of the reaction mixture at 7 to 12 include hydroxides, carbonates and bicarbonates of alkali metals as well as the above-described basic boron compounds. Representative examples thereof include sodium hydroxide, potassium hydroxide, lithium hydroxide, sodium carbonate, lithium carbonate, potassium carbonate, sodium bicarbonate, etc.

The process of the present invention enables to selectively produce 4,4'-dihydroxydiphenyl in good yield by adding the boron compound. In contrast, the prior art process using only a basic substance and adding no boron compounds produces 4,4'-dihydroxydiphenyl, but the yield thereof is low and the amount of polyphenylene oxide by-produced increases.

In the process of the present invention, water is used as a reaction solvent. However, other substrates are not required to be soluble in water, and the reaction system may be a slurry or a suspension. The ingredients of the reaction mixture can be mixed by any suitable manners. In general, an alkylphenol, a surfactant, a copper compound, a basic substance, a boron compound and water are added in an arabitary order to a suitable reactor and the mixture is mixed. In some cases, addition of a part of the copper compound in the course of the reaction gives an increased yield of 4,4'-dihydroxydiphenyl. For example, in conducting the reaction on a large scale, a predetermined amount of the catalyst is separated into two equal portions, and one portion is added at the start of reaction and the other portion is added at one or two hours after the start of the reaction. In conducting the reaction on a large scale, if all of the amount of the catalyst is added at the initiation of the reaction, a large amount of diphenoquinone is sometimes contained in the reaction product. In such cases, formation of diphenoquinone can be prevented by separately adding the catalyst. The catalyst is not necessarily separated into two equal portions, but may be separated into any portions, preferably two to four equal portions.

The oxidizing agent which can be used in the process of the present invention is oxygen or an oxygen-containing gas such as air. The oxidizing agent is used in an amount sufficient to convert the starting alkylphenol to an oxidative coupling product, i.e., 0.2 to 0.5 mol, preferably 0.25 to 0.30 mol, as $O_2$ per mol of phenol. If the oxidizing agent is used in an amount more than the upper limit of the above-described range, the proportion of diphenoquinone in the reaction product increases and the proportion of the desired product, 4,4'-dihydroxydiphenyl, decreases. Oxygen or an oxygen-containing gas may be directly introduced into the reaction mixture, or the reaction may be conducted under the atmosphere thereof, but the former provides better results. In the case of using air as oxygen-containing gas, application of pressure serves to accelerate the reaction rate to provide practical results.

In the light of reaction rate, the reaction temperature is desirably kept at 40° to 100° C., preferably 50° to 90° C. If the temperature is lower than 100° C., the reaction rate decreases so that the reaction time must be prolonged.

The time required to complete the reaction depends upon reaction pressure, reaction temperature and amounts of alkylphenol and copper compounds used. However, if the reaction is conducted, for example, under atmospheric pressure using an oxygen gas, the reaction is usually completed within about 6 hours.

The present invention is now illustrated in greater detail by reference to the following examples which, however, are not to be construed as limiting the present invention in any way.

EXAMPLE 1

6.10 g (50 mmols) of 2,6-xylenol, 1.00 g (2.6 mmols) of borax, 0.03 g of sodium laurylsulfate and 30 g of ion-exchanged water were added to a 300 ml, four-necked flask, and the flask was equipped with a thermometer, a Dimroth condenser, a gas-introducing pipe and a stirring blade. Oxygen gas was introduced into the resulting mixture while stirring at about 1,000 rpm, and the mixture was heated to 80° C. When the temperature of the mixture reached 80° C., stirring was once discontinued, and 0.5 ml (0.002 mmol) of cupric acetate was quickly added thereto in the form of an aqueous solution (4.0 mmols/liter), followed by again stirring the mixture. At this point, pH of the reaction mixture was 9.4. Stirring of the mixture and introduction of oxygen were continued for 4 hours while keeping the temperature of the reaction mixture at 80° C.

The reaction mixture was cooled and the pH of the reaction mixture was measured. The pH was 9.0. 4 ml of a 3N HCl aqueous solution was added thereto to acidify. When the mixture was subjected to gas cromatograph according to internal standard method, 4.86 g of 3,3',5,5'-tetramethyl-4,4'-dihydroxydiphenyl (hereinafter abbreviated as "TMDDP") was produced and 0.67 g of 2,6-xylenol was unreacted. Part of the solid product was collected and analyzed by spectrophotometry. As a result, 0.4% of diphenoquinone was contained.

COMPARATIVE EXAMPLE 1

For the purpose of comparison, reaction was conducted according to Example 1 described in Japanese Patent Application (OPI) No. 65834/78 using the copper-amine complex except for employing an ordinary reactor and a stirring apparatus in place of the special wrinkled Morton flask and a stirrer with a Labline type, cruciform, stainless steelmade runner in the following manner.

0.40 g (2.0 mmols) of copper acetate, 0.24 g (4.0 mmols) of ethanolamine and 25 g of ion-exchanged water were added to a first flask.

48.8 g (400 mmols) of 2,6-xylenol, 0.2 g of sodium laurylsulfate and 150 g of ion-exchanged water were added to a 500 ml, four-necked flask, and the flask was equipped with a thermometer, a gas-introducing pipe, a Dimroth condenser and a stirring blade. The mixture was stirred at about 1,000 rpm, and the copper-amine complex solution in the first flask was added thereto, followed by stirring for 15 minutes. An aqueous solution of 0.67 g of sodium bicarbonate was dropwise added thereto over 3 minutes. At this point, the reaction mixture had a pH of 8.5.

The reaction mixture was then heated to 80° C., and an oxygen gas was introduced thereinto for 6 hours under stirring.

The reaction mixture was cooled and the pH thereof was measured. As a result, the pH was 4.0. The mixture was subjected to gas chromatograph according to internal standard method. 30.5 g of TMDDP was produced and 14.6 g of 2,6-xylenol was unreacted. Part of the solid product was collected and analyzed by spectrophotometry. As a result, 0.6% diphenoquinone was contained.

While the conversion of 2,6-xylenol and the yield of TMDDP in Example 1 were 89.0% and 80.3%, respectively, the conversion of 2,6-xylenol and the yield of TMDDP in Comparative Example 1 were 70.0% and 63.0%, respectively. It is apparent from this that, in the case of using no special apparatuses, the process of the present invention is superior to that described in Japanese Patent Application (OPI) No. 65834/78.

EXAMPLE 2

6.10 g (50 mmols) of 2,6-xylenol, 0.31 g (5.0 mmols) of boric acid, 0.10 g (2.5 mmols) of sodium hydroxide, 0.03 g of sodium laurylsulfate and 30 ml of ion-exchanged water were added to the same reactor as used in Example 1. An oxygen gas was introduced into the mixture while stirring at about 1,000 rpm, and the mixture was heated to 80° C. When the temperature reached 80° C., stirring was once discontinued, and 0.5 ml (0.002 mmol) of cupric acetate was quickly added thereto in the form of an aqueous solution (4.0 mmols/liter), followed by again stirring the mixture. At this point, pH of the reaction mixture was 9.5. Stirring of the mixture and introduction of the oxygen gas were continued for 4 hours while keeping the temperature of the reaction mixture at 80° C.

The reaction mixture was cooled and the pH thereof was measured. As a result, the pH was 9.0. 4 ml of 3N HCl aqueous solution was added thereto to acidify, and the mixture was subjected to gas chromatograph according to internal standard method. 4.22 g (69.8%) of TMDDP was produced and 1.70 g (27.9%) of 2,6-xylenol was unreacted. Part of the solid product was collected and analyzed by spectrophotometry. As a result, 0.3% diphenoquinone was contained.

COMPARATIVE EXAMPLE 2

6.10 g (50 mmols) of 2,6-xylenol, 0.40 g (10 mmols) of sodium hydroxide, 0.03 g of sodium laurylsulfate and 30 ml of ion-exchanged water were added to the same reactor as used in Example 1. An oxygen gas was introduced into the mixture while stirring at about 1,000 rpm, and the mixture was heated to 80° C. When the temperature reached 80° C., stirring was once discontinued, and 0.5 ml (0.002 mmol) of cupric acetate was quickly added thereto in the form of an aqueous solution (4.0 mmols/liter), followed by again stirring the mixture. At this point, pH of the reaction mixture was 11.4. Stirring of the reaction and introduction of the oxygen gas were continued for 4 hours while keeping the temperature of the reaction mixture at 80° C.

The reaction mixture was cooled and the pH thereof was measured. As a result, the pH was 9.4. 4 ml of a 3N HCl aqueous solution was added thereto to acidify. The mixture was subjected to gas chromatography by internal standard method. 1.43 g (23.6%) of TMDDP was produced and 2.06 g (33.8%) of 2,6-xylenol was unreacted. Part of the solid product was collected and analyzed by spectrophotometry. As a result, 0.1% of diphenoquinone was contained.

As is apparent from the comparison between the results of Example 2 and that of Comparative Example 2, the conversion of 2,6-xylenol and the yield of TMDDP are low if the boron compound is not present.

EXAMPLE 3

54.4 g (400 mmols) of 2,3,6-trimethylphenol, 8.0 g (21 mmols) of borax, 0.24 g of sodium laurylsulfate and 240 ml of ion-exchanged water were added to a 500 ml, four-necked flask, and the flask was equipped with a thermometer, a Dimroth condenser, a thermometer and a gas-introducing pipe. An oxygen gas was introduced into the mixture while stirring at about 1,000 rpm, and the mixture was heated to 80° C. When the temperature of the mixture reached 80° C., stirring was once discontinued, and 3.6 ml (0.036 mmol) of cupric acetate was quickly added thereto in the form of an aqueous solution (10 mmols/liter), followed by again stirring the mixture. At this point, pH of the reaction mixture was 9.6. Introduction of the oxygen gas and stirring of the mixture were continued for 5 hours while maintaining the temperature of the reaction mixture at 80° C. The reaction mixture was cooled and the pH thereof was measured. As a result, the pH was 8.9. 15 ml of a 3N HCl aqueous solution was added thereto to acidify, and solids produced were collected by filtration. The solids were washed with a hot water of about 80° C. and then washed with toluene to remove unreacted 2,3,6-trimethylphenol. The solids were sufficiently dried to obtain 42.4 g of a white powder. Spectrophotometry of the powder showed that diphenoquinone was not contained and 100% 2,2',3,3',5,6'-hexamethyl-4,4'-dihydroxydiphenyl (hereinafter abbreviated as HMDDP) was contained. The yield of HMDDP was therefore 78.5%.

EXAMPLE 4

6.10 g (50 mmols) of 2,6-xylenol, 1.00 g (2.6 mmols) of borax, 0.03 g of sodium laurylsulfate and 30 ml of ion-exchanged water were added to the same reactor as used in Example 1. Introduction of an air into the mixture was initiated while stirring at about 1,000 rpm, and the mixture was heated to 80° C. When the temperature reached 80° C., stirring was once discontinued, and 1.0 ml (0.01 mmol) of cupric acetate was quickly added thereto in the form of an aqueous solution (10 mmols/liter), followed by again stirring the mixture. At this point, pH of the reaction mixture was 9.3. Stirring of the mixture and introduction of the air were continued for 6 hours while keeping the temperature of the reaction mixture at 80° C.

The reaction mixture was cooled and the pH thereof was measured. As a result, the pH was 9.0. 2 ml of a 3N HCl aqueous solution was added thereto to acidify the reaction mixture. Gas chromatograph of the product according to internal standard method showed that 3.44 g (56.9%) of TMDDP was produced and 1.98 g (32.5%) of 2,6-xylenol was unreacted. Spectrophotometry of a part of the solid product showed that diphenoquinone was not contained.

EXAMPLE 5

97.6 g (800 mmols) of 2,6-xylenol, 16.0 g (42.5 mmols) of borax, 0.48 g of sodium laurylsulfate, 480 ml of ion-exchanged water and 1.6 ml (0.016 mmol) of a cupric acetate aqueous solution (10 mmols/liter) were added to a 1 liter SUS autoclave equipped with a pressure gauge, a safety valve, a gas-introducing inlet, a gas-discharging outlet and an induction stirring apparatus. The gas-discharging outlet was equipped with a pressure-control valve so as to keep the pressure in the system at 4.0 kg/cm² in gauge pressure and always discharge a constant volume of air therethrough. Air of 4.2 kg/cm² in gauge pressure was introduced into the autoclave through the gas-introducing inlet, and the reaction mixture was heated to 80° C. while stirring at about 1,000 rpm. Stirring of the mixture and introduction of air were continued for 1 hour at 80° C. In this situation, a part of the gas in the reaction system was always discharged through the gas-discharging outlet to keep the inner pressure at 4.0 kg/cm² in gauge pressure.

Stirring of the mixture and introduction of air were once discontinued, and the pressure in the autoclave was reduced to atmospheric pressure. Then, 0.8 ml (0.008 mmol) of the same cupric acetate aqueous solution described above was added, and air was again introduced thereinto so that the inner pressure was 4.0 kg/cm² in gauge pressure, followed by continuing the stirring and the introduction of air for 5 hours. During this operation, a constant volume of gas was discharged through the gas-discharging outlet.

Stirring of the mixture and introduction of air were discontinued, and the pressure in the autoclave was reduced to atmospheric pressure. Then, 30 ml of a 3N HCl aqueous solution was added thereto to acidify the reaction mixture, followed by collecting solids by filtration. The solids were washed with a hot water of about 80° C. and then washed with toluene to remove unreacted 2,6-xylenol and polyphenylene oxide. The solids were sufficiently dried to obtain 71.1 g of a yellow powder. Spectrophotometry of a part of the powder showed that the powder contained 0.8% of diphenoquinone and 99.2% of TMDDP. Thus, the yield of TMDDP was 72.9%.

While the invention has been described in detail and with reference to specific embodiment thereof, it will be apparent to one skilled in the art that various changes and modifications can be made therein without departing from the spirit and scope thereof.

What is claimed is:

1. A process for producing 4,4′-dihydroxydiphenyls comprising dimerizing alkylphenols represented by the formula:

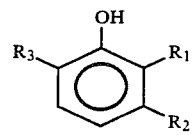

wherein $R_1$ and $R_3$ each represents a straight or branched chain alkyl group having 1 to 12 carbon atoms and $R_2$ is a hydrogen atom or a straight or branched chain alkyl group having 1 to 12 carbon atoms, in an aqueous solution of pH 7 to 12 containing a surfactant in the presence of an oxidizing agent selected from the group consisting of oxygen and an oxygen-containing gas, said dimerization being conducted at 40°–100° C. in the presence of a copper compound selected from the group consisting of halides, basic halohydroxides, carboxylates, sulfates, nitrates, alkylsulfates, arylsulfates, carbonates, basic carbonates, hydroxides and chlorates of copper, and a material selected from the group consisting of (a) a basic boron compound selected from the group consisting of lithium metaborate, sodium metaborate, sodium perborate, lithium tetraborate, borax, trimethoxyborane and triphenoxyborane, and (b) a mixture of a basic substance selected from the group consisting of hydroxides, carbonates and bicarbonates of alkali metals and a boron compound selected from the group consisting of boric acid, boron oxide, lithium metaborate, sodium metaborate, sodium perborate, lithium tetraborate, borax, trimethoxyborane and triphenoxyborane.

2. The process of claim 1, wherein the alkylphenols are selected from the group consisting of 2,6-xylenol, 2-methyl-6-butylphenol, 2,6-diethylphenol, 2,6-diisobutylphenol, 2-methyl-6-octylphenol, 2-isobutyl-6-dodecylphenol, 2,6-di-tert-butylphenol, 2,6-di-sec-butylphenol, 2-cyclohexyl-6-methylphenol, 2,3,6-trimethylphenol, 2,3,6-triethylphenol, 2,6-dimethyl-3-ethylphenol, 2,3-diethyl-6-tert-butylphenol and 2,6-di-tert-butyl-3-methylphenol.

3. The process of claim 1, wherein the surfactant is an organic compound having both a hydrophobic group and a hydrophilic group in the molecule.

4. The process of claim 1, wherein the organic compound is selected from the group consisting of alkylsulfonates, alkylbenzenesulfonates, alkylnaphthalenesulfonates, alkylsulfate, alkyl ether sulfates, alkyl phosphates and alkyl ether phosphates.

5. The process of claim 1, wherein the surfactant is used in an amount of 0.05 mmol per mol of the alkylphenols.

6. The process of claim 1, wherein the oxidizing agent is used in an amount of 0.2 to 0.5 mol as $O_2$ per mol of the alkylphenols.

7. The process of claim 1, wherein the copper compound is used in an amount of 0.01 to 0.1 mmol per mol of the alkylphenols.

8. The process of claim 1, wherein the basic substance is selected from the group consisting of sodium hydroxide, potassium hydroxide, lithium hydroxide, sodium carbonate, lithium carbonate, potassium carbonate and sodium bicarbonate.

9. The process of claim 1, wherein the basic boron compound or the mixture of basic substance and boron compound is used in an amount such that the pH of the reaction mixture is maintained at 7 to 12.

* * * * *